(12) United States Patent
Nesland, Sr. et al.

(10) Patent No.: US 10,976,231 B2
(45) Date of Patent: Apr. 13, 2021

(54) HYDRAULIC AND LUBRICATING FLUID CONTAMINATION SENSOR SYSTEM

(71) Applicant: Fluidmatics, LLC, Gig Harbor, WA (US)

(72) Inventors: Nickolas Bernheart Nesland, Sr., Gig Harbor, WA (US); Mark Allen Conover, Bellingham, WA (US)

(73) Assignee: Fluidmatics, LLC, Gig Harbor, WA (US)

( * ) Notice: Subject to any disclaimer, the term of this patent is extended or adjusted under 35 U.S.C. 154(b) by 691 days.

(21) Appl. No.: 14/996,322

(22) Filed: Jan. 15, 2016

(65) Prior Publication Data

US 2016/0209314 A1 Jul. 21, 2016

Related U.S. Application Data

(60) Provisional application No. 62/188,993, filed on Jul. 6, 2015, provisional application No. 62/104,555, filed on Jan. 16, 2015.

(51) Int. Cl.
| | | |
|---|---|---|
| *G01L 15/00* | (2006.01) | |
| *G01N 15/06* | (2006.01) | |
| *G01N 33/28* | (2006.01) | |
| *G01N 15/00* | (2006.01) | |

(52) U.S. Cl.
CPC ......... *G01N 15/06* (2013.01); *G01N 33/2888* (2013.01); *G01N 2015/0053* (2013.01)

(58) Field of Classification Search
CPC ..................................................... G01N 15/06
USPC ....................................................... 73/53.07
See application file for complete search history.

(56) References Cited

U.S. PATENT DOCUMENTS

| | | | |
|---|---|---|---|
| 4,898,078 A | 2/1990 | Gage et al. | |
| 5,239,861 A | 8/1993 | Fujita et al. | |
| 6,619,112 B2 * | 9/2003 | Juhasz | ................... B01D 46/44 |
| | | | 73/168 |
| 2010/0182591 A1 | 7/2010 | Chambon et al. | |
| 2014/0233605 A1 * | 8/2014 | Rasor | ................. G01N 33/2841 |
| | | | 374/142 |

FOREIGN PATENT DOCUMENTS

| | | |
|---|---|---|
| DE | 19751180 C1 | 2/1999 |
| EP | 2 302 223 A1 | 3/2011 |
| EP | 2574905 A1 | 4/2013 |
| GB | 2 234 519 A | 2/1991 |

OTHER PUBLICATIONS

International Search Report and Written Opinion dated Mar. 28, 2016, issued in corresponding International Application No. PCT/US2016/013677, filed Jan. 15, 2016, 9 pages.

* cited by examiner

*Primary Examiner* — Jamel E Williams
(74) *Attorney, Agent, or Firm* — Forge IP, PLLC

(57) ABSTRACT

A method and apparatus for maintaining the rate of flow of hydraulic or lubricating fluid through a particle contamination sensor or monitor at an acceptable level is disclosed. The rate of flow may be a specific value or lie within a desired range of values. Regardless, maintaining the rate of flow at an acceptable level improves the accuracy of information produced by the contamination sensor or monitor. A display for displaying the particle information created by a particle contamination sensor or monitor in a manner more easily understood by maintenance personnel and a method of creating such a display is also disclosed.

16 Claims, 6 Drawing Sheets

HYDRAULIC AND LUBRICATING FLUID CONTAMINATION SENSOR SYSTEM

CROSS-REFERENCES TO RELATED APPLICATIONS

This application claims the benefit of U.S. Provisional Application No. 62/188,993, filed on Jul. 6, 2015, and U.S. Provisional Application No. 62/104,555, filed on Jan. 16, 2015, the disclosures of both of which are incorporated herein by reference in their entirety.

BACKGROUND

As is well known to those familiar with hydraulic and lubricating fluids, solid particle contaminants (hereinafter also "particle contaminants" or just "contaminants") in such fluids have a detrimental effect on the systems and devices that use such fluids, such as hydraulic control systems, hydraulic machines and motors, internal combustion engines, etc. Solid particle contamination of hydraulic and lubricating fluids degrades such fluids, leading to the failure of the systems and devices that use the fluids. Solid particle contaminated hydraulic and lubrication fluids can cause internal leakage, which can lower the efficiency of the systems or devices employing such fluids. Further, solid particle contaminated hydraulic and lubricating fluid can impact the ability of valves to control fluid flow and fluid pressure. Parts can stick to one another and seize when large amounts of contaminants accumulate. As a result, it is desirable and often necessary to regularly test hydraulic and lubricating fluid for particle contaminants.

Testing can be done by withdrawing a small amount of fluid, transferring the fluid to a testing laboratory, and testing the fluid for contaminants. While usable, this procedure is both time consuming and expensive and, therefore, generally unacceptable. This procedure is also unacceptable due to the time delay between fluid withdrawal and fluid testing. During this period of time, the system or device from which the fluid is withdrawn can be harmed if the fluid is contaminated.

As a result, machine installable contamination sensors have been developed. Testing is accomplished by installing one or more contamination sensors or monitors on a system or device employing hydraulic or lubricating fluid. An example of a contamination sensor is the Hydac International CS 1000 Series Contamination Sensor. An example of a contamination monitor is the Schroeder Testmate® Contamination Monitor. The CS 1000 Series Contamination Sensor and the Schroeder Testmate® Contamination Monitor as well as other types of particle contamination sensors and monitors measure solid particle contamination, usually optically, in hydraulic and lubricating fluid and output information regarding the amount of particles in the fluid. The particle information may be presented in various sizes, such as >4, >6 and >14 microns. The measurement results are provided according to various standards, such as International Standards Organization (ISO) Code 4406 and SAE Aerospace standard AS4059, for example.

One of the major disadvantages of current hydraulic and lubricating fluid contamination sensor systems is the need to maintain the flow of the fluid being monitored through the sensor either constant or at least within an acceptable range. If the flow is not maintained constant or within an acceptable range, the particle information provided by the sensor becomes inaccurate. This can result in the inability to promptly alert users to the occurrence of unacceptable particle contamination of the monitored hydraulic or lubricating fluid.

Another major disadvantage is the difficulty of easily interpreting the results quickly and accurately either locally or remotely by maintenance personnel that are often unfamiliar with the nuances of the chosen output.

SUMMARY

Disclosed is a method and apparatus for maintaining the rate of flow of hydraulic or lubricating fluid through a particle contamination sensor or monitor at an acceptable level. The rate of flow may be a specific value or lie within a desired range of values. Regardless, maintaining the rate of flow at an acceptable level improves the accuracy of information produced by the contamination sensor or monitor.

Also disclosed is a display for displaying the particle information created by a particle contamination sensor or monitor in a manner more easily understood by maintenance personnel and a method of creating such a display.

BRIEF DESCRIPTION OF THE DRAWINGS

The foregoing aspects and many of the attendant advantages of the disclosed subject matter will become more readily appreciated as the same become better understood by reference to the following detailed description, when taken in conjunction with the accompanying drawings, wherein.

EXEMPLARY EMBODIMENTS

Figure 1:
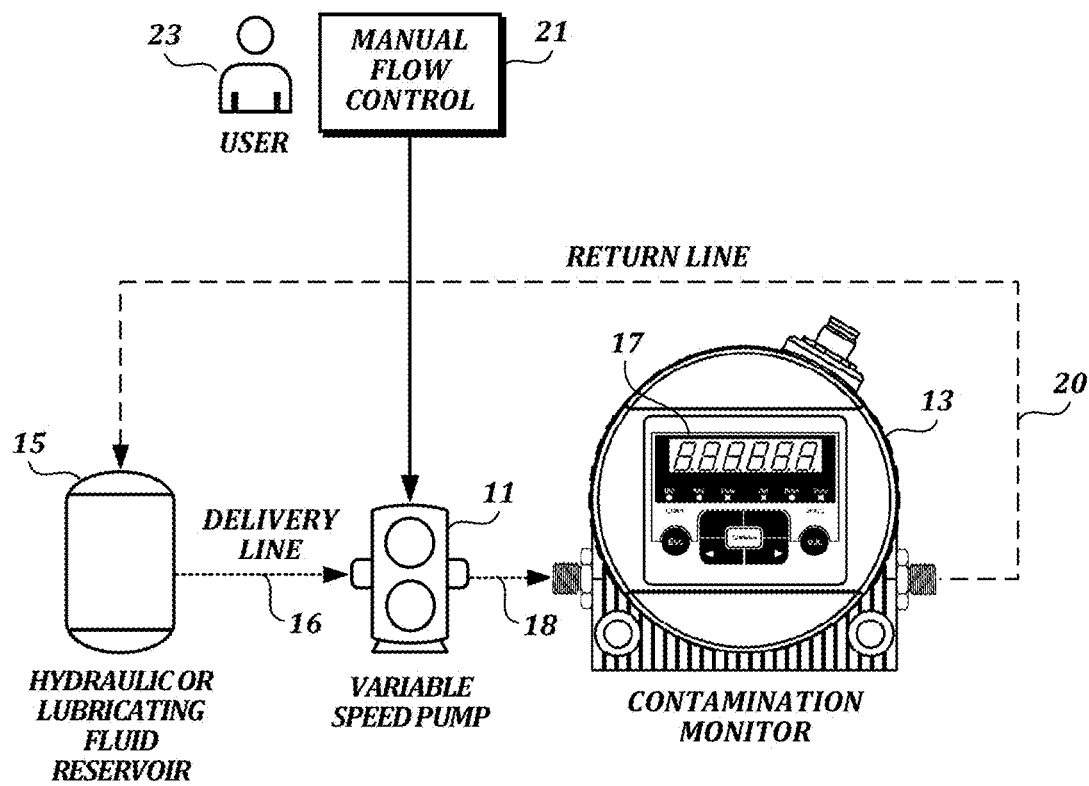
FIG. 1 is a pictorial diagram of an exemplary hydraulic and lubricating fluid contamination sensor system.

FIG. 1 is a pictorial diagram of an exemplary hydraulic and lubricating fluid contamination sensor system. More specifically, FIG. 1 includes a variable speed pump 11 and a contamination monitor 13 connected in seriatim to a hydraulic and lubricating fluid reservoir 15 via a delivery line or conduit 16. The hydraulic and lubricating fluid reservoir 15 represents a generic source of a hydraulic and lubricating fluid whose solid particle contaminant content is to be monitored. By way of example only, the reservoir 15 could be the oil reservoir of a hydraulic system, or the crank case of an internal combustion engine, either gasoline or diesel. Regardless of the nature of the hydraulic and lubricating fluid reservoir 15, the reservoir is connected to the input of the variable speed pump 11 via the delivery line 16. The output of the variable speed pump 11 is connected to the input of the contamination monitor via a suitable conduit 18.

The output of the contamination monitor is connected to the hydraulic or lubricating fluid reservoir 15 via a return line or conduit 20.

Since it is not important to the disclosed hydraulic and lubricating fluid contamination sensor system, the hydraulic or other system, gasoline or diesel engine or other system, apparatus, or device that incorporates the reservoir 15 is not disclosed. Further, as will be better understood from the following discussion, rather than a fluid reservoir, the variable speed pump 11 could receive fluid whose particle contamination content is to be monitored from some other source, such as a line of a hydraulic system. The fluid delivery and return lines or conduits 16 and 20 and, thus, the variable spaced pump 11 and contamination monitor 13 could parallel an operational line of a hydraulic or other system, apparatus, or device.

One example of a suitable variable speed pump is the FG Series Pump-Motor Unit available from Fluid-O-Tech International Inc., Plantsville, Conn. This exemplary pump-motor unit includes an analog voltage control input. The magnitude of the analog voltage controls the speed of the motor and, thus, the fluid flow rate through the motor pump unit. See Appendix A of Provisional Application No. 62/104,555, the subject matter of which is incorporated herein by reference, for more detail regarding this exemplary variable speed motor pump unit.

One example of a suitable contamination monitor is the Hydac International CS 1000 Series Contamination Sensor available from Hydac Filtertechnik GmbH, Saar, Germany. See Appendix B of Provisional Application No. 62/104,555, the subject matter of which is incorporated herein by reference, for more detail regarding this exemplary contamination monitor. The CS 1000 Series Contamination Sensor, which is illustrated in FIG. 1, includes a display 17 that, depending on the display state of the monitor, can display any one of a plurality of parameters including, but not limited to, ISO particle count, SAE particle count, and flow rate.

Also illustrated in FIG. 1 is a manual flow control 21 and a user 23. The manual flow control 21 is connected to the variable speed pump 11. In the case of the exemplary FG Series Pump-Motor Unit, the manual flow control 21 can be a simple rheostat operated by the user 23 to control the voltage applied to the control input of this exemplary variable speed pump 11. Obviously, other types of variable speed pumps may require a different type of manual flow control.

In operation, the contamination monitor is placed in its flow display state. As necessary, the user 23 operates the manual flow control 21 to change the speed of the variable speed pump 11 until the displayed flow is at a predetermined value or falls within a predetermined range, as appropriate. The contamination monitor is then changed to the ISO or SAE particle display state to display the particle contamination state of the hydraulic or lubricating fluid pumped through the contamination monitor 13 by the variable speed pump 11. Because the flow is maintained at a predetermined value or within a predetermined range, the accuracy of the ISO or SAE particle display is maintained valid.

Figure 2:
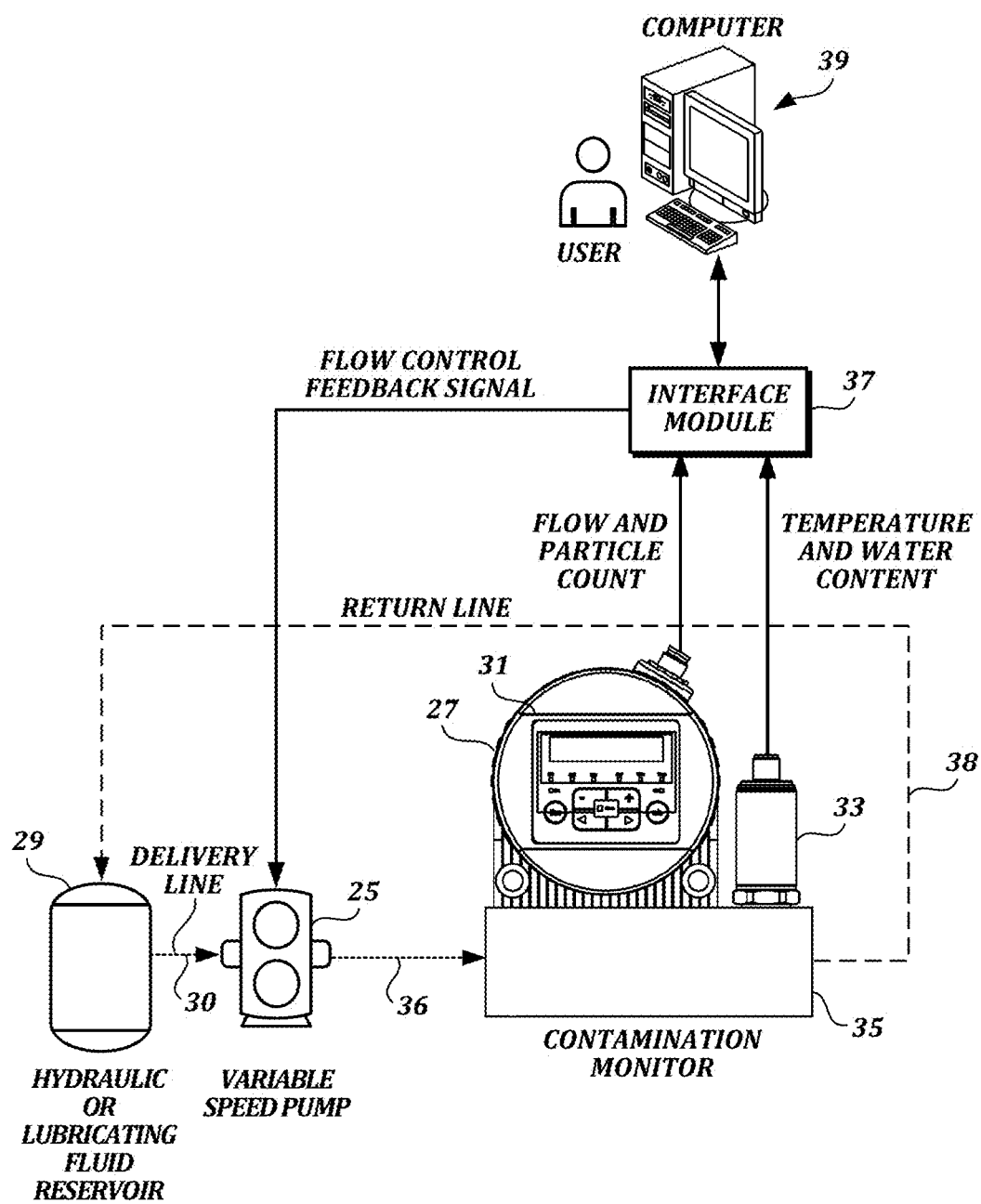
FIG. 2 is a pictorial diagram of another exemplary hydraulic and lubricating fluid contamination sensor system.

Like the embodiment illustrated in FIG. 1, the embodiment illustrated in FIG. 2 includes a variable speed pump 25 and a contamination monitor 27. The variable speed pump is connected to a hydraulic or lubricating fluid reservoir 29 via a delivery line or conduit 30 and pumps fluid to the contamination monitor 27. While the variable speed pump 25 is similar to the variable speed pump 11 illustrated in FIG. 1, the contamination monitor 27 illustrated in FIG. 2 is shown mounted on a support block 35. Such an arrangement is shown in Appendix B of Provisional Application No. 62/104,555, which has been incorporated herein by reference. The hydraulic or lubricating fluid pumped by the variable speed pump 25 is supplied to the support block 35 via an input line or conduit 36. The support block 35 supplies the fluid to the contamination monitor 27. Fluid is returned to the reservoir 29 via a return line or conduit 38. Also mounted on the support block 35 is an aqua sensor 33. An exemplary aqua sensor is the AS1000 AquaSensor available from Hydac International, which is described in Appendix C of Provisional Application No. 62/104,555, the subject matter of which is also incorporated herein by reference. Like the contamination monitor 27, the aqua sensor 33 receives fluid from the support block 35.

The contamination monitor 27 includes a display 31 and may be the same as the contamination monitor 13 shown in FIG. 1. An electrical output of the contamination monitor 27 that is connected to an interface module 37 provides information to the interface module 37 that is similar to an information displayed by the display 31. An electrical output of the aqua sensor 33 is also connected to the interface module 37.

While various information signals are produced by the contamination monitor 31 and the aqua sensor 33, only the ones of importance to this disclosure are discussed here. These are the signals that contain flow and particle count information produced by the contamination monitor and temperature and water content information produced by the aqua sensor. As noted above, these signals are sent to the interface module 37. The interface module is connected to a computer or other signal interpretation device 39. The computer can be a desktop computer (illustrated) or a laptop computer or some specialized programmable or programmed computing device that includes a display.

In addition to receiving information signals, the interface module generates a flow control feedback signal that is applied to the control input of the variable speed pump 25. Either based on the program of a microprocessor included in the interface module 37 or in response to instructions received from a program installed on the computer 39, the interface module analyzes the flow information received from the contamination monitor 27 and controls the flow control feedback signal such that the flow passing through the contamination monitor is maintained at an acceptable constant value or within an acceptable predetermined range.

Figure 3:
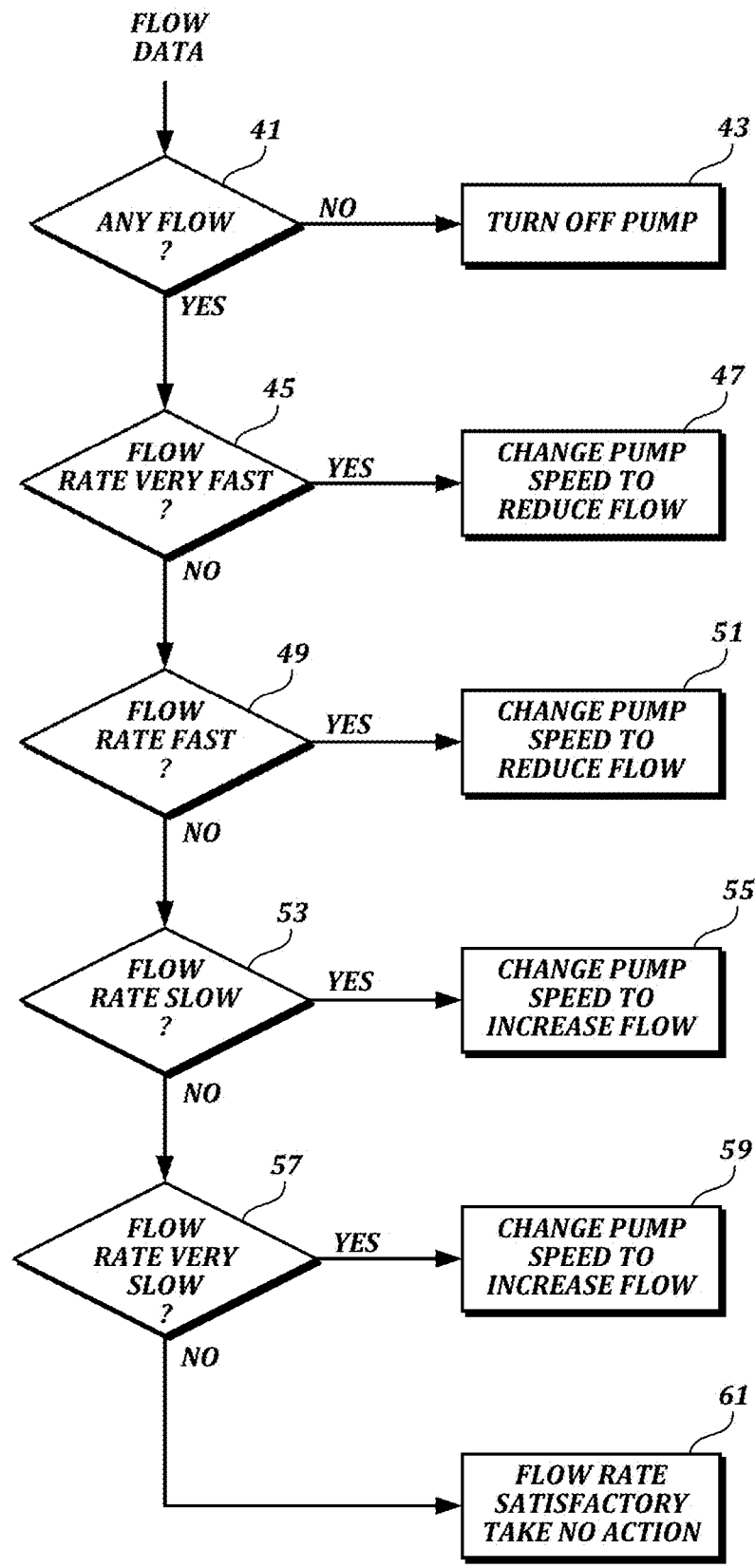
FIG. 3 is a functional flow diagram of an exemplary way of creating a flow control feedback signal suitable for use in the hydraulic and lubricating fluid contamination sensor systems shown in FIGS. 2 and 5.

FIG. 3 is a functional flow diagram of an exemplary way of creating a flow control feedback signal suitable for use in FIG. 2 provided by either the interface module 37 or the computer 39 depending upon how the FIG. 2 embodiment is implemented. In general, the flow portion of the flow and particle data received from contamination monitor 27 is analyzed in a series of tests. In accordance with results of the tests, the speed of the variable speed pump 25 is controlled. Controlling the speed of the variable speed pump controls the rate of fluid flow through the contamination monitor 31. Five sequential tests are included in FIG. 3, the order of which can be changed if desired. The first test 41 determines if there is any fluid flow. If there is no fluid flow, power to the variable speed pump is turned off 43. No fluid flow indicates a problem with the system, such as a lack of fluid. As a result, the variable speed pump is shut down. If fluid is flowing, next, a test 45 is made to determine if the rate of flow is very fast. If so, the pump's speed is changed (reduced) so as to reduce the flow 47 to an acceptable level. If the flow rate is not very fast, next, a test 49 is made to determine if the flow rate is fast, but not very fast. If the flow rate is fast, the pump's speed is again changed (reduced) so as to reduce the flow 51 to an acceptable level. Next, if the flow rate is not fast, a test 53 is made to determine if the flow rate is slow. If the flow rate is slow, the pump's speed is changed (increased) to increase the rate of flow 55 to an acceptable level. If the flow rate is not slow, next a test 57 is made to determine if the flow rate is very slow. If the flow rate is really slow, the pump's speed is changed (increased) to increase the rate of flow 59 to an acceptable level. If the flow rate is not very slow, the flow rate is deemed to be at an acceptable level and no action is taken 61.

As will be understood from the foregoing description, the embodiment illustrated in FIG. 2 includes an automatic feedback control system that eliminates the need for a user to manually control the flow of fluid passing through the contamination monitor 35 in order to maintain the flow at an acceptable constant value or within an acceptable range.

Figure 4:
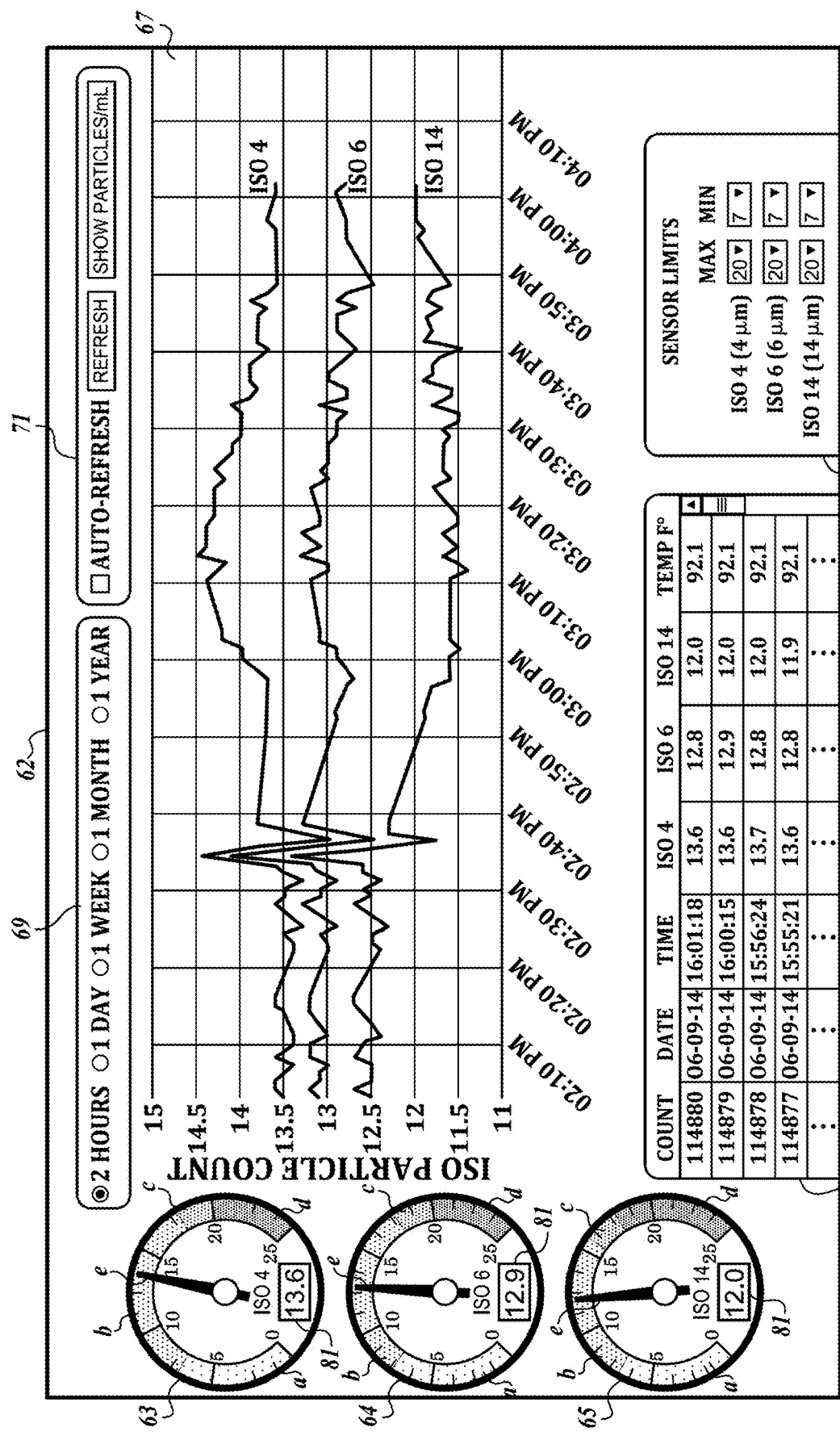
FIG. 4 is a pictorial diagram of an exemplary display suitable for use in the hydraulic and lubricating fluid contamination sensor systems shown in FIGS. 2 and 5.

Returning to FIG. 2, the display of the computer 39 displays the information produced by the contamination monitor 31 and the aqua sensor 33 including, but not limited to, flow and particle count information and temperature and water content information. An exemplary computer display 62 suitably for use in FIG. 2 is illustrated in FIG. 4. If the display is to be transmitted to a remote location, it may be in the form of a web page.

The display illustrated in FIG. 4 includes a plurality of regions. On the left side is a vertical array of three rotary widget dials 63, 64, and 65. The operation of the rotary widget dials are controlled by software widgets. Software widgets are small computer applications that have limited functionality. Widget displays, as shown in FIG. 4, normally occupy a small area of web page (display) and display information fetched from other locations, e.g., web sites. Widgets are usually created in DHTML or Adobe Flash.

Across the top, above a graph 67, is a horizontal list of time increments 69. In this exemplary display, the illustrated time increments are two hours, one day, one week, one month, and one year. As noted by the circles located to the left of each of these intervals, the intervals are selectable with the two-hour interval being selected in FIG. 4 as shown by the dark dot inside the circle. Only one interval is selectable at a time. The chosen interval controls the time interval of the graph 67. The time interval is located on the horizontal axis of the graph 67. Selection is done in accordance with conventional computer control technology using a mouse, stylus, etc.

To the right of the time increment list 69 is an auto-refresh selection area 71, which allows the graph to be automatically refreshed if an auto-refresh element is selected. Again, selection is accomplished in any conventional, well-known computer control technology manner.

The graph 67 is a three-element running graph that shows particle counts over the chosen time interval, two hours in the illustrated example. One graph element is designated ISO 4, the second graph element is designated ISO 6, and the third graph element is designated ISO 14. The numbers 4, 6, and 14 relate to particle count in microns based on ISO standards. ISO particle count value is shown on the vertical axis of the graph 67, on the left side thereof.

The graph element identifiers are also associated with the three widget dials 63, 64, and 65 located on the left side of FIG. 4 with ISO 4 associated with the upper dial 63, ISO 6 associated with the middle dial 64, and ISO 14 associated with the lower dial 65, as shown by the related ISO 4, ISO 6, and ISO 14 identifiers on the widget dials.

Located beneath the graph 67 is a table area 73 that includes a plurality of columns. The first (leftmost) column is designated a COUNT column, the second column moving to the right is designated a DATE column, the third column is designated a TIME column, the fourth column is designated ISO 4, the fifth column is designated ISO 6, and the sixth column is designated ISO 14. The seventh or last column is designated temperature in degrees Fahrenheit (TEMP F°). The COUNT column is a vertical seriatim list of numbers used to identify the information in the other columns. The DATE column sets forth the date when a particular count was recorded, the TIME column designates the time when a particular count was recorded. The ISO 4, ISO 6, and ISO 14 columns contain the particle values measured when the particular count was recorded. The TEMP F.° column provides information about the temperature of the hydraulic or lubrication fluid when a particular count was recorded.

Located to the right of the table 73 is a sensor limits box 75. The sensor limits box sets forth the maximum and minimum values for the ISO 4, ISO 6, and ISO 14 data that produce the count values shown in the table 33.

In operation, obviously, the table 67 provides a running ISO particle count value of the sensed ISO 4, ISO 6, and ISO 14 data. The widgets receive the same information or data and the rotary widget dials 63, 64, and 65 display the data in an instantaneous manner. As illustrated by stippling, the widget dials include various color-coded areas located in an arc. In one exemplary embodiment, a very low particle area (a) is gray, followed by a green area (b), followed by a yellow area (c), followed by a red area (d). Each area relates to a range of particle count values starting with zero at the beginning end of the gray (a) area and ending at 65 at the ending end of the red (d) area. A needle (e) that moves across a dial, in a conventional manner, points to the actual particle count. In addition to the value being shown by the needle/dial combinations, a numerical value is shown in a box 81 included at the bottom of each of the rotary widget dials 63, 64, and 65.

As will be readily appreciated from the foregoing description, when the widget dial arrows are in the gray (a) or green (b) areas, the ISO particle count is acceptable. When in the yellow (c) area, the ISO count is still acceptable, but less than desirable. When in the red (d) area, the ISO particle count is unacceptable.

In addition to providing the display shown in FIG. 4, text or e-mail messages can be provided to a user access device or some other suitable alert device when an ISO count reaches the red area of one of the widget dials.

As will be readily appreciated by those skilled in the art, the display illustrated in FIG. 4 should be considered as exemplary and not as limiting. The layout of the various components of the display can be arranged differently. Some components may be deleted and others added depending on the needs of the end user.

Figure 5:
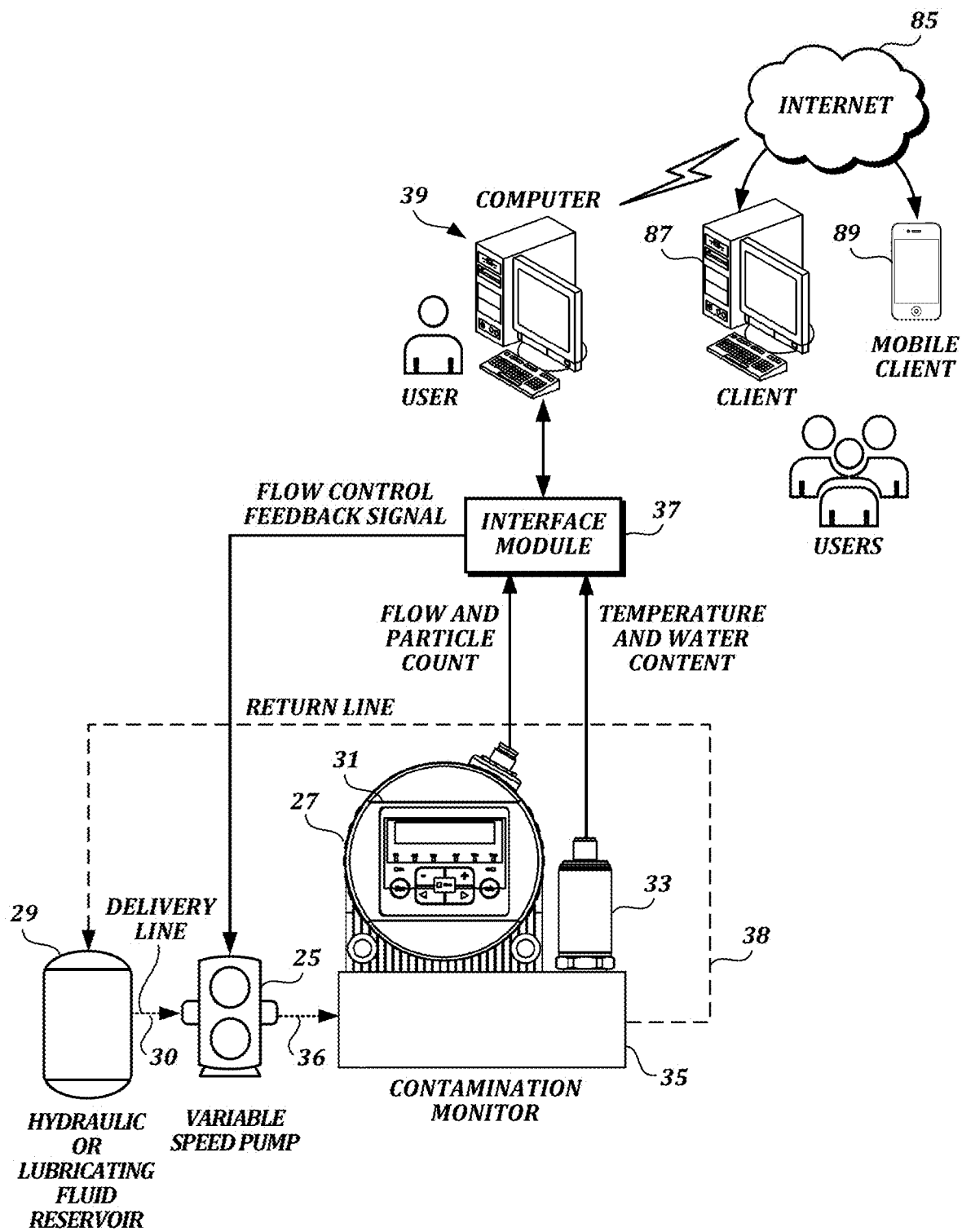
FIG. 5 is a pictorial diagram of an exemplary remote hydraulic and lubricating fluid contamination sensor system.

The embodiment illustrated in FIG. 5 includes all of the elements of the embodiment illustrated in FIG. 2, plus remote display and control devices. More specifically, the computer 39 is illustrated as connected via a network, such as the Internet 85, to remote display and control devices such as a client desktop computer 87 or a client mobile device 89, which can take the form of a smart phone, a personal digital assistant, a laptop computer, etc. The information received by the computer 39 illustrated in FIG. 1 is transmitted to the remote devices via the Internet 85. This allows remotely located users to monitor the operation of the contamination monitor 27 and control the flow control feedback signal, if needed, by changing the acceptable constant value or the acceptable range, as also can be done by the computer 39.

Figure 6:
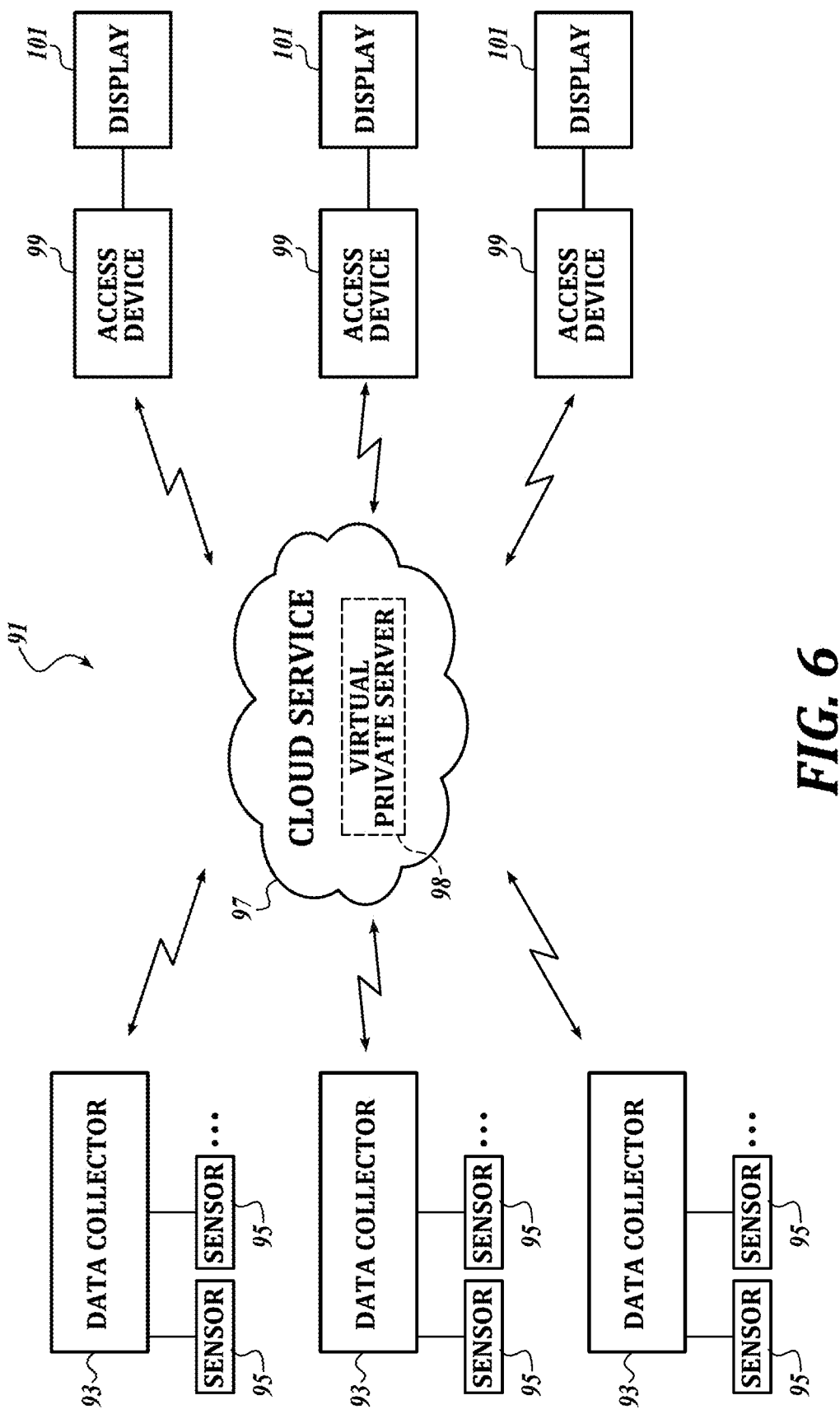
FIG. 6 is a block diagram of an exemplary remote oil contamination sensor system for use with multiple sensors located on the same or different apparatus.

FIG. 6 is a block diagram of an exemplary remote oil contamination sensor system 91 suitable for monitoring a plurality of devices that use hydraulic or lubricating fluid, or a plurality of regions of a single device. The results are remotely displayable on a single or a plurality of monitoring devices. More specifically, the illustrated remote oil contamination sensor system 91 comprises: a plurality of data collectors 93; a plurality of fluid particle sensors 95; a cloud service 97; and a plurality of access devices 99, each of which includes a display 101. The plurality of data collectors 93 and particle sensors 95, which are shown in block form in FIG. 6, may be formed by elements connected to the computer 39 shown in FIGS. 2 and 5, for example.

One or more of the particle contamination sensors 95 are connected to each of the data collectors 93. More specifically, depending on implementation, a single particle contamination sensor 95 may be connected to a single data collector 93. Such an implementation might be used when a particle contamination sensor is associated with a single hydraulic system or a single device that employs hydraulic or lubricating fluid. Alternatively, in other implementations, a plurality of particle contamination sensors 95, each associated with a single hydraulic system or device, may be connected to a single data collector 95. Such an embodiment might be used with a large hydraulic system or device so that hydraulic or lubricating fluid contamination can be detected at various locations. Still further, each of the particle contamination sensors 95 can be associated with a separate hydraulic system or device. As a result, FIG. 6 should be taken as exemplary and not limiting.

Data produced by the particle contamination sensors 95 is collected by the related data collector 93. While, preferably, data is collected at regular intervals, if desired, the collection intervals can vary in time. For example, the collection intervals can be different when the associated hydraulic system or device is running, as opposed to when idled or shut down. While the particle contamination sensors 95 are illustrated as "hard wired" to their related data collectors 93, obviously the sensors can be wirelessly connected, if desired. While the data collectors 93 can take on various forms, in one actual embodiment of the disclosed subject matter, the data collectors are formed by local processors, specifically, a small computer running a Linux operating system. For example, the computer 39 shown in FIG. 5.

The cloud service 97 is a conventional cloud service comprised of a plurality of servers formed by one or more server farms. As is well known to those skilled in the art, a cloud service can provide virtual private servers to users of the cloud service, one of which 98 is associated with the disclosed subject matter and shown in FIG. 6. In one actual embodiment of the disclosed subject matter, the virtual private server 98 included in the cloud service and associated with the disclosed subject matter is a virtual private server running a Linux operating system.

While a hard wire connection could be made between the data collectors and the cloud service, preferably, as illustrated, the connection is a wireless connection. More specifically, the connection between the data collectors 93 and the cloud service can be a WiFi connection, a wired Internet connection, a cell phone signal connection (GSM, CDMA, and LTE), or any other wired or wireless data connection known in the art.

The access devices 99 can take any one of a plurality of forms, personal computer (desktop or laptop), personal digital assistant (PDA), cell phone, etc. Regardless of the nature of a specific access device, each of the illustrated access devices includes or is connected to a display 101.

In operation, each of the data collectors 93 collect data from the one or more particle contamination sensor 95 connected to the data collector. The collected data is formatted in a conventional data format, such as the ISO 4406:99 data format. That is, as shown in FIG. 4 and previously described, the data may be tabulated in the ISO form of A, B, and C, where A represents the number of particles greater than 4 microns, B represents the number of particles greater than 6 microns, and C represents the number of particles greater than 14 microns. In essence, the data collectors convert current sensor data into a form suitable for creating a more user friendly display, such as the display illustrated in FIG. 4 and described above. The data collectors 93 transmit the collected, converted data to the virtual private server 98 included in the cloud service 97. The virtual private server stores the received data, thereby making this collected data available for retrieval by the access devices 99. The access devices 99 retrieve the data stored on the virtual private server and use the retrieved data to create a user friendly display, an example of which is illustrated in FIG. 4 and described above.

As will be readily appreciated from the foregoing description, both the local and remote hydraulic/lubricating contamination sensor systems and methods described above, in addition to providing contamination information in real time, provide the information in a form that is readily usable by maintenance and other personnel unfamiliar with the nuances of ISO and other standard codes. In essence, the oil contamination sensor system includes local processors that collect data from one or more particle counters mounted in machines being monitored. The particle count data is in ISO 4406 or some other standard code. In the illustrated FIG. 2-6 embodiments, the particle data falls in three categories designated ISO 4, ISO 6, and ISO 14, where the 4, 6, and 14 refer to the size of the particles in microns being counted. The local processor stores the received data and transmits it to a larger storage device, such as a virtual private server included in a cloud service, presumably at regular intervals. The data is presented to the end user as a display, in preferably a remotely transmittable Web page display that contains widgets. While shown as rotary display widgets, obviously, the widget displays can take on other forms— linear, for example. If desired, the display or Web page can include other information, such as the collected ISO code data and graphs. The end result is an oil contamination sensor system that provides data in a relatively simple and easily understood form to a remote location, i.e., a location remote from the system or device whose hydraulic or lubrication fluid is being monitored. In this regard, "remote" should be construed broadly and include, for example, a location in the same building as the system or device including a location near the system or device. In such environments, the cloud service shown in FIG. 6 may not be required. Rather, data from the data collectors may be presented directly to the access device wirelessly or via wires, encrypted or unencrypted as desired. In addition to presenting contamination data in a relatively easy-to-understand form, if desired, text and/or e-mail messages can be sent to an end user when particle contaminants are at or approaching a critical stage. Further, information in addition to that shown in FIG. 4 can be displayed either or both as widget (instantaneous) data or running data, such as temperature, moisture content, or saturation level, for example. Max/min values can also be displayed for such other data. While preferred embodiments have been illustrated and described, it will be appreciated that various changes can be made therein without departing from the spirit and scope of the disclosed subject matter.

The embodiments of the invention in which an exclusive property or privilege is claimed are defined as follows:

1. A fluid contamination monitor system comprising:
a variable speed pump that receives fluid whose particle contamination is to be monitored and supplies the fluid to a contamination monitor at a controllable rate of flow;
a contamination monitor that receives the fluid whose particle contamination is to be monitored from said variable speed pump, said contamination monitor generating information regarding the rate of flow of the fluid received from the variable speed pump and displaying information regarding the particle contamination of the fluid; and
a controller that controls the operation of the variable speed pump so as to keep the rate of flow at a target level.

2. The fluid contamination sensor system as claimed in claim 1, wherein the target level lies within a range of values.

3. The fluid contamination monitor system as claimed in claim 1, wherein said target level is a predetermined value.

4. The fluid contamination monitor system as claimed in claim 1, wherein said controller manually controls the operation of the variable speed pump in accordance with user input.

5. The fluid contamination monitor system as claimed in claim 1, wherein the contamination monitor produces information indicating the rate of flow of the fluid received from said variable speed pump and the controller receives the rate of flow information and includes a program that controls the operation of the variable speed pump so as to keep the rate of flow at said target level.

6. The fluid contamination monitor system as claimed in claim 1, including a display that displays information regarding the particle contamination of the fluid.

7. The fluid contamination monitor system as claimed in claim 6, wherein the display includes a plurality of elements each displaying the level of contamination of particles having a size greater than a predetermined value.

8. The fluid contamination monitor system as claimed in claim 1, wherein the fluid comprises at least one of a hydraulic fluid and a lubricating fluid.

9. A method of determining the particle contamination of a fluid, comprising the steps of:
controlling the rate of flow of the fluid whose particle contamination is to be monitored such that the rate of flow is at a target level; and monitoring the flow of fluid whose rate is controlled and producing information regarding the particle contamination of the fluid.

10. The method of determining the particle contamination of a fluid as claimed in claim 9, wherein the target level lies within a range of values.

11. The method of determining the particle contamination of a fluid as claimed in claim 9, wherein the target level is a predetermined value.

12. The method of determining the particle contamination of a fluid as claimed in claim 9, wherein the rate of flow of the fluid whose particle count is to be monitored is manually controlled by a user.

13. The method of determining the particle contamination of a fluid as claimed in claim 9 further comprising the steps of producing information regarding the rate of flow of the fluid whose particle contamination is to be monitored and automatically controlling the rate of flow based on said information.

14. The method of determining the particle contamination of a fluid as claimed in claim 9, further comprising the step of displaying information regarding the particle contamination of the fluid whose particle contamination is to be monitored.

15. The method of determining the particle contamination of a fluid as claimed in claim 14, wherein the displaying step comprises the step of displaying a plurality of regions, each region displaying the level of contamination of particles having a size greater than a predetermined value.

16. The method of determining the particle contamination of a fluid as claimed in claim 9, wherein the fluid comprises at least one of a hydraulic fluid and a lubricating fluid.

* * * * *